United States Patent [19]

Neidleman et al.

[11] 4,246,347

[45] Jan. 20, 1981

[54] PROCESS FOR THE PRODUCTION OF FRUCTOSE

[75] Inventors: Saul L. Neidleman, Oakland; William F. Amon, Jr., Danville; John Geigert, Clayton, all of Calif.

[73] Assignee: Cetus Corporation, Berkeley, Calif.

[21] Appl. No.: 88,103

[22] Filed: Oct. 24, 1979

Related U.S. Application Data

[63] Continuation-in-part of Ser. No. 39,337, May 16, 1979, and a continuation-in-part of Ser. No. 42,219, May 29, 1979.

[51] Int. Cl.³ ............................................. C12P 19/02
[52] U.S. Cl. ........................................ 435/105; 536/1
[58] Field of Search ............................ 435/105; 536/1

[56] References Cited

U.S. PATENT DOCUMENTS

| | | | |
|---|---|---|---|
| 3,050,444 | 8/1962 | Holstein et al. | 195/31 |
| 3,868,304 | 2/1975 | Messing | 195/31 |

OTHER PUBLICATIONS

Ruelius et al., Biochem. Biophys. Acta, vol. 167, pp. 493–500, (1968).
Volc et al., Folia Microbiol., vol. 23, pp. 292–298, (1978).

*Primary Examiner*—Lionel M. Shapiro
*Attorney, Agent, or Firm*—Fitch, Even, Tabin, Flannery & Welsh

[57] ABSTRACT

A process is described for the production of fructose from glucose. An aqueous solution of glucose is converted to D-glucosone by an enzymatic process. D-glucosone is then converted to substantially pure fructose by chemical hydrogenation. Fructose may be recovered in crystalline form.

14 Claims, 4 Drawing Figures

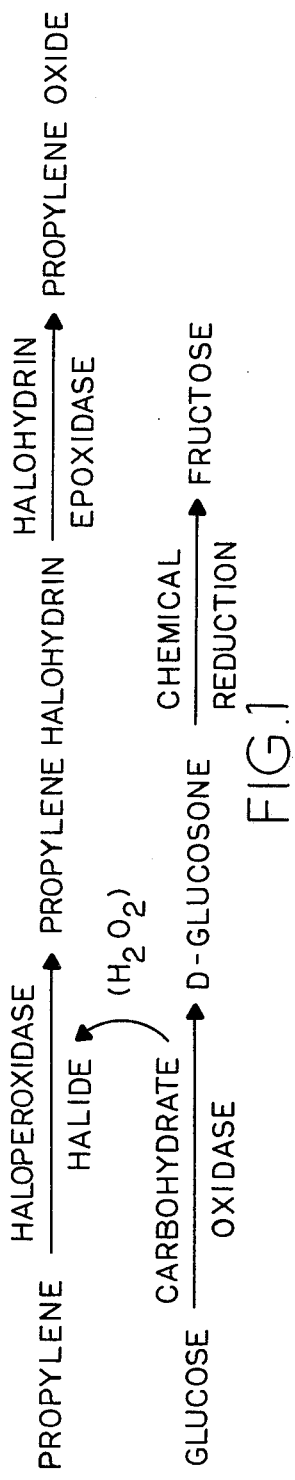
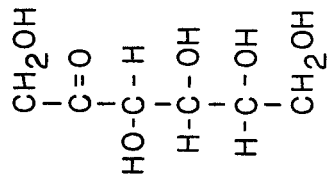
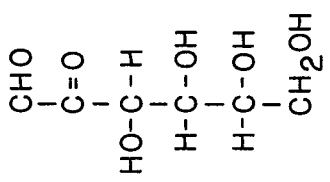
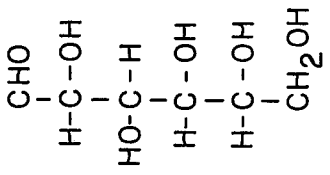

PROCESS FOR THE PRODUCTION OF FRUCTOSE

This application is a continuation-in-part of Applications Ser. No. 39,337 filed May 16, 1979, and Ser. No. 42,219 filed May 29, 1979.

This invention relates generally to the production of crystalline fructose from glucose by way of a two-step process: enzymatic oxidation followed by chemical hydrogenation. This process provides a novel approach for the production of crystalline fructose without the necessity for physical separation of the residual glucose starting material.

The unique physical, chemical, and metabolic properties of crystalline fructose present specialty application possibilities not feasible with glucose isomerase-produced high fructose corn syrup (HFCS), which typically contains 42% fructose, 50% dextrose and 8% polysaccharides. While HFCS is about as sweet as sucrose, crystalline fructose is about 50% sweeter and can be used at lower levels to give the same sweetness. HFCS competes primarily on a direct-cost basis with liquid sugars in a variety of traditional food uses in either dry or liquid form, primarily in pharmaceutical applications and in foods where reduced calories per unit of sweetness is desired. Crystalline fructose is used in dietetic candy and ice cream and can advantageously supplement or replace glucose, sucrose or HFCS in beverages.

The production of crystalline fructose on a commercial scale has been confronted with a number of serious problems. A major one of these problems is manufacturing cost. The only commercially feasible production method up to the present invention was based on first producing a glucose-fructose syrup mixture from glucose (employing either glucose isomerase or alkaline isomerization) or sucrose (via invert sugar), then physically separating the two sugars (ion exchange or selective calcium salt precipitation) and, finally, recovering the fructose from the aqueous solution in crystalline form (seeding or methanol precipitation).[1] The physical separation treatment of the two sugars is needed because crystalline fructose is at best difficult, and frequently impossible, to recover from aqueous solution unless substantially all ionic substances, residual glucose and other contaminants are removed.[15] Such treatment is costly and therefore results in a high market price for fructose—a price which is not competitive with cane sugar as a food source.

[1]*Specialized Sugars for the Food Industry*, edited by Jeanne C. Johnson, Noyes Data Corporation, 1976, pp. 130–201.
[15]U.S. Pat. No. 3,050,444; A.G. Holstein (1962).

The literature teaches that low levels of fructose can be made from glucosone. As early as 1889, fructose was formed by reduction of D-glucosone with zinc dust in aqueous acetic acid.[6] This reduction has been employed as an analytical test for the detection of D-glucosone in several biological materials.[8,10,12] Reduction of D-glucosone to D-fructose has also been accomplished with sodium borohydride.[13] Conversion of D-glucosone to fructose is a feasible enzymatic reaction since reductases which carry out the reduction of —CHO→—CH₂OH are known.[14]

[6]*Advances in Carbohydrate Chemistry*, Vol. II, edited by M.L. Wolfrom, 1956, pp. 43–96.
[8]C. Berkeley, *Biochem. J.*, 27, 1357 (1933).
[10]R.C. Bean and W.Z. Hassid, *Science*, 124, 171 (1956).
[12]J. Volc, M. Wurst and V. Musilek, *Folia microbial*, 23, 448 (1978).
[13]B.N. White and R. Carubelli, *Carbohydr. Res.*, 33, 366 (1974).
[14]*Microbial Transformation of Non-Steroid Cyclic Compounds*, edited by K. Kieslich, Georg Threme Publishers, Stuttgart, 1976, pp. 279–280.

The literature also teaches that low levels of glucosone can be made from glucose. Several methods of oxidizing glucose have been reported—with $H_2O_2$[4] or with copper acetate.[5] In each of these reactions, conversion yields are low (<30%) and many side-products arise. Glucose has been converted to D-glucosone by first preparing a derivative of the glucose (e.g. by reacting with phenyl hydrazine to make glucosazone[6] or reacting with p-toluidine[7]) and then chemically treating that derivative to yield D-glucosone. In these reactions, yields were no higher than 50%, and the unrecoverable reagents are too expensive for commercial use. In addition, the use of aromatic-containing reagents could pose problems in achieving food grade quality sugars.

[4]R. Selby, M.A. Morrell and J.M. Crofts, *J. Chem. Soc.*, 75, 787 (1899).
[5]W.L. Evans, W.D. Nicoll, G.C. Strouse and C.E. Waring, *J. Amer. Chem. Soc.*, 50, 2267 (1928).
[6]*Advances in Carbohydrate Chemistry*, Vol. II, edited by M.L. Wolfrom, 1956, pp. 43–96.
[7]H.J. Hass and P. Schlimmer, *Liebigs Ann. Chem.*, 759, 208 (1972).

Conversion of glucose to D-glucosone is also a known enzymatic reaction. As early as 1932, glucose was reported to be oxidized to D-glucosone by the crystalline style of a mollusca, *Saxidomus giganteous*.[8] In 1937, D-glucosone was reported to be formed by the oxidation of glucose, starch, maltose or sucrose with plasmolysed preparations of two molds, *Aspergillus parasiticus* and *Aspergillus flavus-oryzae*[9]. In 1956, the enzymatic oxidation of glucose to glucosone was reported in a red alga, *Iridophycus flaccidum*.[10] A carbohydrate oxydase was isolated from mycelius of the Basidiomycete, *Polyporus obtusus*, which oxidized glucose to D-glucosone.[11] No mention was made of yields. Finally, in 1978, glucose-2-oxidase activity was detected in the basidiomycete,

[9]C.R. Bond, E.C. Knight and T.K. Walker, *Biochem J.*, 31, 1033 (1937). *Oudemansiella mucida*, as well as other wood-rotting fungi.[12] The best yield reported was no higher than 50%. In all of these cases D-glucosone production, it is believed, is accompanied by generation of hydrogen peroxide.
[8]C. Berkeley, *Biochem. J.*, 27, 1357 (1933).
[10]R.C. Bean and W.Z. Hassid, *Science*, 124, 171 (1956).
[11]F.W. Janssen and H.W. Ruelius, *Biochem.Biophys. Acta*, 167, 501 (1968).
[12]J. Volc, M. Wurst and V. Musilek, *Folia microbial*, 23, 448 (1978).

One of the objects of the present invention is to provide an improved method for producing substantially pure fructose from glucose.

Another object of the present invention is to provide a fructose-making process in which the costly physical separation of residual glucose from fructose or from a fructose-rich syrup is unnecessary.

A further object of the invention is to provide a process by which pure fructose may be made from glucose in an economical and commercially feasible way.

Other objects of the present invention will become apparent from the following description and examples, and with reference to the accompanying drawings wherein:

FIG. 1 is a schematic diagram of a preferred example of the method of the invention;

FIG. 2 is a representation of the molecular structure of D-glucose;

FIG. 3 is a representation of the molecular structure of D-glucosone; and

FIG. 4 is a representation of the molecular structure of D-fructose.

With respect to the molecular structure of D-glucosone, it will be recognized by those skilled in the art that several other forms of the molecule have been postulated to exist in aqueous solution. A number of these are cyclic.[2,3]

[2]C.R. Becker and C.E. May, *J. Amer. Chem. Soc.*, 71, 1491 (1949).
[3]F. Petuely, *Monatsch.fur Chem.*, 83, 765 (1952).

As used herein, the terms "glucose", "D-glucose" and "dextrose" are employed interchangeably to embrace this monosaccharide in any form—solution or dry. FIG. 2 represents glucose.

As used herein, the terms "D-glucosone" and "D-arabino-2-hexosulose" are employed interchangeably. FIG. 3 represents D-glucosone.

As used herein, the terms "fructose", "D-fructose" and "levulose" are employed interchangeably to refer to the isomer of glucose that is sweeter than glucose. The term "crystalline fructose" is used in this application to embrace this monosaccharide in anhydrous form. FIG. 4 represents fructose.

According to the present invention, generally stated, glucose in aqueous solution is enzymatically converted to D-glucosone with an appropriate enzyme such as carbohydrate oxidase or glucose-2-oxidase. This conversion is allowed to proceed spontaneously, rapidly and substantially completely. D-glucosone, without prior isolation, is then converted to fructose by suitable chemical hydrogenation. This conversion is also allowed to proceed rapidly and essentially completely. The resulting fructose, substantially free of glucose and all other saccharides, is recovered either as an aqueous solution or in solid form.

As mentioned and referenced above, low level conversions of glucose to D-glucosone and of D-glucosone to fructose are known in the scientific literature, but the concept of coupling these two reactions to produce fructose from glucose has not been obvious to others. In addition, the successful use of these two reactions to produce crystalline fructose from glucose in an economic, commercially useful process has not been reported prior to our invention. In neither the reported conversion of glucose to D-glucosone nor the reported conversion of D-glucosone to fructose, was the concept of producing crystalline fructose from glucose considered. D-glucosone was chemically synthesized because it was desired as a chemical standard. D-glucosone was discovered in biological systems, either unintentionally (e.g. as an unknown component in a biochemical pathway under study) or intentionally (e.g. as part of an investigation of the bio-chemical oxidation of glucose in blood). D-glucosone was reduced to fructose as an analytical spot test for the presence of D-glucosone.

Unless both the conversion of glucose to D-glucosone and the conversion of D-glucosone to fructose are accomplished in high yield, the industrial production of crystalline fructose by this method would be prohibitive since the costly physical separation treatment to remove residual glucose would still be needed. According to the present invention, glucose is readily and completely converted to D-glucosone using a purified oxidoreductase enzyme such as carbohydrate oxidase or glucose-2-oxidase. The yield obtained in the present invention exceeds that reported in the literature for this enzyme. This high conversion to D-glucosone eliminates the need to physically separate any residual unconverted glucose.

Certain oxidoreductases have catalytic activity with respect to oxidizing the hydroxyl group on the second carbon of glucose, promoting oxidation of that hydroxyl group to a keto group, for example converting the structure of FIG. 2 to that of FIG. 3. The specific oxidoreductase enzymes described in the examples herein are referred to variously as "glucose-2-oxidase", "pyranose-2-oxidase", and "carbohydrate oxidase", but the invention is not necessarily limited to enzymes so designated. Glucose-2-oxidase possesses a high specificity for glucose as a substrate, whereas carbohydrate oxidase, while having glucose as its preferred substrate, has a broader substrate specificity. Any enzyme capable of converting the hydroxyl group on the second carbon of glucose to a keto group and not otherwise substantially affecting the remainder of the glucose molecule falls within the scope of our invention. Such an enzyme may be specified as one which has glucose-2-oxidase activity.

A preferred carbohydrate oxidase enzyme is derived from the microorganism *Polyporus obtusus*. Sources of glucose-2-oxidase include several other microorganisms, mollusca and red alga referred to above. These enzymes and their sources are merely indicative and are not intended to be all-inclusive of suitable enzymes and their sources within the scope of this invention.

For ease of discussion, various aspects of the present invention will be described with particularity, but not exclusivity, in connection with the use of the preferred carbohydrate oxidase of *Polyporus obtusus* and the glucose-2-oxidase of *Aspergillus oryzae*. The microorganisms may be grown in agitated, submerged culture at room temperature by conventional methods. The enzyme is prepared from the mycelia of the microorganism grown under agitated, submerged culture conditions.

The enzyme is preferably used in an immobilized form, although free enzyme can also be used. The processes for enzyme immobilization are familiar to those skilled in the art, and consist of reacting a solution of the enzyme with one of a broad range of surface treated or untreated organic and inorganic supports. Included among these are polyacrylamide, ethylenemaleic acid copolymers, methacrylic-based polymers, polypeptides, styrene-based polymers, agarose, cellulose, dextran, silica, porous glass beads, charcoal or carbon black wood and sawdust, hydroxy apatite and aluminum or titanium hydroxide. Enzymes in this form have increased stability, extended life and usefulness and recoverability. Reactions employing immobilized enzymes may be run in columns or reaction tanks or other suitable reactors.

In addition to the carbohydrate oxidase or glucose-2-oxidase enzymes, a source of oxygen is needed. Also, a method of hydrogen peroxide removal or utilization is required in the reaction to convert glucose to D-glucosone most efficiently. This is because $H_2O_2$ oxidizes certain critical sites on the enzyme molecule, damaging its function. Procedures of hydrogen peroxide removal include (1) decomposition by the enzyme, catalase, (2) decomposition by known chemical means, and (3) decomposition by using decomposing matrices such as manganese oxide or carbon black[16,17] as the immobilizing support for the oxidoreductase enzyme. In a preferred alternative method, the hydrogen peroxide produced, rather than being decomposed, may be consumed to produce a valuable co-product. Coupling D-glucosone production with propylene halohydrin or propylene oxide production, in accordance with copending U.S. Patent Applications Ser. No. 39,337 and Ser. No. 42,219, is a preferred example, as shown in FIG. 1.

[16] Z. Diwnjak and M.D. Lilly, *Biotechnology and Bioengineering*, 18, 737–739 (1976).
[17] Y.K. Cho and J.E. Bailey, *Biotechnology and Bioengineering*, 19, 769–775 (1977).

The enzymatic conversion of glucose to D-glucosone is preferably conducted in water at about neutral pH, but can be conducted within the pH range of from about three to about eight with the use of appropriate buffers. This conversion is preferably conducted at ambient temperature, but can be conducted within the temperature range of from about 15° C. to about 65° C. Pressure conditions are preferably atmospheric but can range from below to above atmospheric. Any carbohydrate material, which by chemical or enzymatic means yields glucose, is a suitable source of glucose for conversion to D-glucosone and fructose synthesis. These substances would include, but are not limited to the following: cellulose, starch, sucrose, corn syrup, HFCS and other syrups containing varying proportions of glucose and fructose.

After conversion of substantially all of the glucose to D-glucosone, the D-glucosone is readily and essentially completely converted to fructose using molecular hydrogen and an appropriate catalyst. The catalysts suitable for the second step of this process are any of the well known hydrogenation catalysts. These catalysts comprise one or more metals or metallic compounds having hydrogenation activity. The catalyst may be employed alone or in admixture with promoters. The preferred catalysts are selected from the Group VIII elements of the periodic table. These elements, frequently referred to as the Noble Metals, include nickel, platinum, palladium, rhodium, etc. The most preferred catalysts are palladium and nickel. Other satisfactory catalysts are the metallic elements of Group IB and IIB of the periodic table, including copper and zinc. Transition metals are also satisfactory catalysts for this process. These include chromium, tungsten, and manganese.

The catalysts may be in the form of the catalytic metal or metal compound supported on a solid, inert carrier particle. These supported catalysts are useful for heterogeneous hydrogenations wherein the hydrogen gas and organic feed are contacted over an insoluble form of the catalyst. Suitable carriers include silica, alumina, zirconia, kielsilguhr, carbon, and mixtures thereof.

The preferred catalyst is palladium-on-carbon.

The catalyst may also be in the form of small, insoluble particles which form a slurry in the reaction zone, for example, Raney nickel.

Heterogenous catalysts are generally formed by depositing a salt of the metal, for example, an oxide, carbonate or, hydroxide on the solid carrier. These materials are then converted in situ to the active form of the catalyst. Alternatively the intermediates in this process may be reduced to the final product from using a chemical reducing means. The preferred material for this homogenous reduction is sodium borohydride which must be present in stoichiometric quantities. The hydrogenation may be conducted at ambient temperature and pressure, but can be conducted at higher or lower temperature and pressure.

The assays used for analyzing the sugars of the present invention are given below:

1. Thin layer chromatography (TLC). A vicel coated glass plates are developed with an 8:8:2:4 (by volume); isopropanol:pyridine:acetic acid:water solvent system. Glucose and fructose have $R_f$'s 0.5–0.6; D-glucosone has an $R_f$ 0.4–0.5 streak. ($R_f$=the distance substance migrates from origin/solvent front distance from origin). When the plates are sprayed with triphenyltetrazolium chloride (2% TTC in 0.5 N NaOH), both D-glucosone and fructose instantly yield red spots; glucose yields a red spot only upon heating for ten minutes at 100° C. When the plates are sprayed with diphenylamine/aniline/phosphoric acid/ethyl acetate reagent, (0.15 g/0.8 ml/11 ml/100ml), glucose yields a brown spot; D-glucosone yields a purple streak; and fructose yields a yellow spot upon heating for 10 minutes at 95° C.

2. High performance liquid chromatography (HPLC). A μ-Bondapak-Carbohydrate column, purchased from Waters Associates, is run with 15% aqueous acetonitrile containing 0.001 M potassium phosphate buffer pH7 at a flow rate of 2 ml/min. Glucose has an $R_t$ 11.5, D-glucosone an $R_t$ 14.0, and fructose an $R_t$ 9.5 ($R_t$=retention time). Assays are run on a spectra physics SP8000 instrument using both a Waters Associates refractive index detector and a Schoeffel variable wavelength UV detector set at 192 nm.

3. Mass spectrometry (MS). The following derivatization protocol is used to make the chemical components volatile:

(a) To approximately 100 mg of the lyophilized sample, 110 mg of N,N-diphenylhydrazine (H$_2$NNφ$_2$) and 1 ml of 75% aqueous ethanol are added. The reaction mixture is vortexed and then allowed to sit overnight at room temperature.

(b) 3 ml of water is added to the reaction mixture and the resulting precipitate is separated from the supernatant by centrifuging and decanting. To this precipitate, 1 ml of a 1:1 mixture of pyridine-acetic anhydride is added. The reaction mixture is placed in a 35°–40° C. water bath for 15 minutes, with occasional shaking.

(c) 2 ml of water is added to stop the reaction and then the mixture is extracted 2 times with 3 ml portions of ethyl ether. The ether is dried over a small amount of anhydrous sodium sulfate, then the ether is driven off with gentle heating (−40° C.) and blowing nitrogen.

(d) The resulting solid or syrup is ready for mass spectrometric analysis.

Expected reactions:

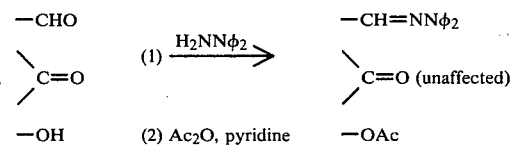

Glucose yields a molecular ion at mass 556 (C$_{28}$H$_{32}$N$_2$O$_{10}$) and a base ion at mass 168 (Nφ$_2$ ion fragment); fructose yields a molecular ion at mass 390 (C$_{16}$H$_{22}$O$_{11}$); D-glucosone yields a molecular ion at mass 512 (C$_{26}$H$_{28}$N$_2$O$_9$) and an intense, diagnostic fragment ion at mass 223 (OC—CH=N—Nφ$_2$ ion fragment). Assays are run on a Finnigan GC/MS/DS Model 4023 instrument set at 70 eV electron impact ionization and at 220° probe temperature.

4. Colorimetric test tube assay. The analysis of D-glucosone in the presence of an excess of glucose is readily determined by two colorimetric methods. Using triphenyltetrazolium chloride (TTC), the detection method is based on a differential rate of reduction by the two sugars. Into a 20 ml test tube is added 0.5 ml sample, plus 0.1 ml 1% aqueous TTC, plus 0.4 ml 6 N NaOH. After exactly 5 min, 15 ml acetic acid:ethanol (1:9) is added and the test tube contents vortexed. With water used as a blank, absorbance is measured at 480 nm, using a Varian 635 UV/VIS spectrometer. Glucose reduces TTC to a red pigment—a triphenylformazan—about 100 times slower than an equivalent amount of D-glucosone. Using diphenylamine/aniline/phosphoric acid reagent, the detection method is based on the different colors produced with sugars of different structures. Into a 20 ml test tube is added 0.2 ml sample, plus 5 ml of the following reagent mix:

| | |
|---|---|
| diphenylamine | 0.15 g |
| aniline | 0.80 ml |
| isopropanol | 100 ml |
| phosphoric acid | 11 ml |

The test tubes are placed in 37° water bath for 60 minutes. Glucose yields a yellow-colored solution; D-glucosone yields a purple-colored solution.

The sources of the pure sugars used in various analytical aspects of the invention are given below:
1. D-glucose was purchased from Applied Science Laboratories, 99% purity,
2. D-fructose was purchased from Applied Science Laboratories, 99+% purity,
3. D-glucosone was chemically synthesized by the following method: 20 g of glucose is mixed with 1 l of distilled water containing 27 ml glacial acetic acid. 44 g of phenylhydrazine is added. The reaction is run for 3 hours at 80° C. with vigorous stirring from a mechanical stirrer and then cooled to room temperature overnight. The solid is filtered and washed with 10% acetic acid, water, and then ethyl ether. The solid is dried well in a vacuum oven at 50° C. Experimental yield is 16.1 g of glucosazone. The glucosazone is placed in a 3-neck, 3-l flask and 450 ml of ethanol, 750 ml of distilled water and 9 ml glacial acetic acid are added. 27.8 g of fresh benzaldehyde is added and brought to reflux with vigorous stirring with a mechanical stirrer. The reaction is refluxed for 5 hours. The condenser is reversed and 450 ml is distilled over, while adding 750 ml of distilled water (via an addition funnel) to the flask. The reaction is cooled overnight to let the benzaldehyde phenylhydrazone precipitate. The solution is filtered and the residue washed with distilled water (~1 l) until the water becomes clear. The filtrate plus washings are concentrated to 500 ml and then extracted with 10 by 300 ml portions of ethyl ether. To get rid of residual ethyl ether in the aqueous solution, it is placed on a rotary evaporator for 30 minutes. The aqueous solution is passed through a 4 by 100 cm column containing rigorously acetone-washed Amberlite XAD-2. The column is washed with an additional 200 ml of water to remove residual glucosone. The combined aqueous portions are lyophilized. Experimental yield of glucosone is 3.4 g (16% overall yield).

The following examples illustrate various features of the invention, but are in no way intended to limit the scope of the invention which is defined in the appended claims. Unless indicated otherwise, all temperatures are at ambient temperature (about 25° C.) and all pressures at ambient room pressure (about 1 atm).

EXAMPLE·I

Substantially complete conversion of glucose to D-glucosone using immobilized carbohydrate oxidase is shown in this example.

Glucose (2 g) is added to 20 ml of distilled water in a 100 ml Pyrex flask and the sugar solution stirred. Oxygen gas is bubbled into the flask and 3 mg of catalase (Sigma Chemical Co., C-40, from bovine liver) is added. Agarose-immobilized carbohydrate oxidase prepared as below from 200 ml of culture is also added to the flask.

To prepare the enzyme, mycelial pads of Polyporus obtusus ATCC#26733 are grown on yeast/malt extract agar slants as follows: yeast extract (3 g), malt extract (3 g), agar (20 g), peptone (5 g) and glucose (10 g) are added to distilled water (1 l) and the pH is adjusted to 6.7. The medium is sterilized at 121° C. for 15 minutes. The pH is then adjusted to 6.4. The organism is inoculated on the agar slants and grown for 7 days at 25° C. The slant-grown organism is then used to inoculate yeast/malt extract medium (20 ml medium in 125 ml Erlenmeyer flask), prepared as above (but no agar added). The organism is grown for 9 days on a rotary shaker at 25° C. The culture is vacuum filtered through #541 Whatman paper in a Buchner funnel. The mycelia, retained on the filter paper, contain the enzyme.

The mycelia obtained from 400 ml of culture are washed twice with 0.05 M potassium phosphate buffer at pH 7.0. The mycelia are then placed in a Waring blender which contains 70 ml of 0.05 M potassium phosphate buffer at 7.0, and then homogenized for 3 minutes. The mixture is then centrifuged at 6000 rpm for 20 minutes and the supernatant decanted from the solids. To the supernatant, placed in a 500 ml Erlenmeyer flask, 19 g of polyethylene glycol (weight 4000) is added and the solution stirred for 30 minutes. The suspension is then centrifuged at 7000 rpm and for 20 minutes. The supernatant is decanted off and discarded. 15 ml of 0.2 M sodium chloride plus 15 ml 0.05 M potassium phosphate buffer at pH 7.0 are then added to the precipitate and vortexed. The solution is allowed to stand for 30 minutes during which time a precipitate forms. The mixture is centrifuged at 14000 rpm for 20 minutes. An opaque white supernatant containing cell-free, purified enzyme is decanted off.

Immobilization of the enzymes on agarose may be accomplished as follows: The cell-free purified enzyme is dialyzed against 500 ml of distilled water overnight. Then 5 ml of 0.1 M sodium bicarbonate at pH 8.0 is added. To this solution, 5 g of Activated CH-Sepharose 4B (washed and reswelled on a sintered glass filter using 500 ml of 1mM HCl) is added. Using an end-over-end mixer, the gel suspension is mixed for 1 hour at 25° C. The gel suspension is then washed first with 40 ml of 0.1 M sodium bicarbonate at pH 8.0, then with 40 ml of 0.05 M Tris buffer at pH 8.0 containing 0.5 M sodium chloride, and then with 0.5 M sodium formate buffer at pH 4.0 also containing 0.5 M sodium chloride.

Samples of the reaction mixture are withdrawn at varying times and analyzed for glucose and D-glucosone. Using HPLC, the peak areas of the peaks at $R_t$ 11.5 min. (glucose) and $R_t$ 14.0 min. (D-glucosone) are quantitated and levels of sugar present calculated. The following results are obtained:

| Reaction Time | Glucose, g | D-Glucosone, g | % of Glucose converted to D-Glucosone |
|---|---|---|---|
| 0 hr | 2.0 | 0.0 | 0 |
| 1 | 1.2 | 0.8 | 40 |
| 2 | 0.5 | 1.5 | 75 |
| 3 | 0.2 | 1.8 | 90 |
| 4 | <0.1 | >1.9 | 99+ |

The substantial conversion of glucose to D-glucosone is also shown by the disappearance of the spot at $R_f$ 0.58 (Glucose) and the appearance of the streak at $R_f$ 0.43–0.49 (D-glucosone) over the course of the reaction, and by the increase in absorbance at 480 nm over the course of the reaction using the TTC colorimetric test tube assay.

That the product is indeed D-glucosone is confirmed by derivatization followed by mass spectrometry as described previously. The diagnostic D-glucosone mass ions at mass 512 (molecular ion) and mass 223 (OC—CH=N—N$\phi_2$ ion fragment) are obtained for the product.

EXAMPLE II

The following example illustrates the chemical conversion of D-glucosone to fructose using various catalysts:

D-glucosone (20 mg) is added to 2 ml of distilled water in a micro-hydrogenator apparatus (Supelco, Inc.). Catalyst (50 ml) is then added and the apparatus is fed hydrogen gas—continuously bubbled if at atmospheric pressure, batch fed if at higher than atmospheric pressure.

After 5 hours, the residual D-glucosone and the produced fructose are analyzed.

Using HPLC, the peak areas of the peaks at $R_t$ 14.0 min. (D-glucosone) and $R_5$ 9.5 min. (fructose) are quantitated and levels of sugar present calculated. The following results are obtained:

| Catalyst[a] | Pressure | % D-glucosone Converted to Fructose |
|---|---|---|
| 5% Ruthenium on Alumina | atmospheric | 40 |
| 5% Rhodium on Carbon | atmospheric | 50 |
| 5% Platinum on Carbon | atmospheric | 60 |
|  | 55 psi | 70 |
| 10% Platinum on Carbon | atmospheric | 75 |
| Platinum Black | atmospheric | 80 |
| Platinum Oxide | 55 psi | 65 |
| 5% Palladium on Carbon | atmospheric | greater than 90 |
|  | 55 psi | greater than 90 |
| Raney Nickel | atmospheric | 30[b] |

The conversion of D-glucosone to fructose is also shown by the disappearance of the streak at $R_f$ 0.43–0.49 (D-glucosone) and the appearance of the spot at $R_f$ 0.52.

That the product is indeed fructose is confirmed by derivatization followed by mass spectrometry as described previously. The diagnostic fructose mass ion at mass 390 (molecular ion) is obtained for the product.

EXAMPLE III

Essentially complete conversion of D-glucosone to fructose under varying hydrogenation conditions is shown in this example.

Reaction A:

D-glucosone (1 g) is added to 200 ml of distilled water in a micro-hydrogenator apparatus. 5% palladium (Pd) on carbon (1 g) is then added and hydrogen gas is continuously bubbled into the vessel at atmospheric pressure and ambient temperature. After 24 hours, additional 5% palladium on carbon (500 mg) as added. The reaction is ended at 30 hours.

Reaction B:

D-glucosone (1 g) is dissolved in 136 ml water and 0.1 g of 5% Pd on carbon is added to the solution. The solution is placed in a pressure vessel equipped with an efficient magnetic carrier. The apparatus is pressured to 500 psig with $H_2$ after the usual removal of air. The vessel is heated to 130° C. while the contents are vigorously stirred. The calculated amount of $H_2$ is taken up in 75 minutes. After removal of catalyst and evaporation of the water in vacuum, a syrupy residue is left. The product is identified as fructose. In addition, the proton NMR spectrum confirms the absence of mannitol and sorbitol, the products of further reduction.

Reaction C:

D-glucosone (2 g) is dissolved in 140 ml 88% aqueous ethanol and reacted as in reaction B. The theoretical amount of $H_2$ is consumed in 16 hours.

The conditions for each reaction and the results obtained are summarized in the following table:

| Reaction | Weight Ratio Catalyst to Glucosone | Solvent | Temp | Pressure psig | Time hr | % Conversion |
|---|---|---|---|---|---|---|
| A | 1.5 | $H_2O$ | 25° | 0 | 30 | 95% |
| B | 0.1 | $H_2O$ | 130° | 625 | 1.25 | 100% |
| C | 0.1 | (88:12) EtOH:$H_2O$ | 130° | 575 | 4 | 100% |

It can be seen that the hydrogenation of D-glucosone to fructose can be conducted under a variety of differing protocols involving changes in temperature, pressure, solvent, reaction time and weight ratio of catalyst to substrate. The palladium catalyst does not further reduce fructose.

EXAMPLE IV

The following represents an example for essentially complete conversion of glucose to fructose by the action of immobilized carbohydrate oxidase, followed by chemical reduction.

Glucose (1 g) is added to 50 ml of distilled water in a 250 ml Pyrex flask and the sugar solution stirred. Agarose-immobilized carbohydrate oxidase, prepared as in Example I from 50 ml of cell-free, purified enzyme, is then added to the flask, along with 1 mg of catalase (as in Example I).

Eighteen hours later the aqueous solution is decanted from the solids. Analysis of this solution shows that 99+% of the glucose has been converted to D-glycosone.

The aqueous solution is placed in a 100 ml Pyrex flask and stirred. 1 g of 5% palladium on carbon catalyst is added and hydrogen gas bubbling started.

After 24 hours, the aqueous solution is filtered from the solids using Whatman #1 filter paper and Celite filtering aid. Analysis shows that it consists of greater than 95% fructose.

EXAMPLE V

This example shows the production of crystalline fructose from glucose.

The enzymatic conversion of glucose to D-glucosone and the chemical reduction of D-glucosone to fructose yields the aqueous solution of Example IV. This aqueous filtrate is evaporated to dryness under vacuum at 45° C. A white solid material results which rapidly turns into a gummy residue.

This residue is dissolved in 10 ml of hot ethanol, and then the solution is allowed to cool at room temperature for 5 days. White, crystalline material results having the same physical properties (i.e. appearance, melting point and optical rotation) as crystalline fructose; it is crystalline fructose.

EXAMPLE VI

This example shows essentially complete enzymatic conversion of glucose to D-glucosone using glucose-2-oxidase.

The reaction and conditions of Example I (using agarose as the immobilizing support) are repeated substituting glucose-2-oxidase for carbohydrate oxidase. After 5 hours of reaction, more than 99% of the glucose was converted to D-glucosone.

To prepare the enzyme, glucose-2-oxidase, mycelial cultures of *Aspergillus oryzae* ATTC#7252 are grown in beef, yeast extract/tryptone medium as follows: beef extract (5 g), yeast extract (5 g), tryptone (3 g), dextrose (1 g) and Difco starch (24 g) are added to distilled water (1 l) and the pH adjusted to 7.3. The medium is sterilized at 121° C. for 35 minutes. Using spores obtained in a generally known manner, the medium is inoculated to obtain about $3 \times 10^4$ spores/ml and grown on a rotary shaker (180 rpm) at 30° C. for 2 days. The culture is vacuum filtered through #541 Whatman paper in a Buchner funnel and washed several times with water. The mycelia, retained on the filter paper, contain the enzyme.

Purification and immobilization of the enzyme can then proceed using the procedure of Example I.

The D-glucosone can then be chemically converted to fructose using the procedure of Example III.

EXAMPLE VII

In Example I, the level of free hydrogen peroxide generated by the reaction of glucose with *carbohydrate oxidase* in conjunction with D-glucosone formation was minimized by using catalase to decompose the hydrogen peroxide. An alternative method of minimizing the level of free hydrogen peroxide is to couple its production to a hydrogen peroxide-utilizing reaction yielding a desirable (valuable) co-product.

In this example, hydrogen peroxide production is coupled to the production of propylene bromohydrin, an intermediate in propylene oxide synthesis according to concepts detailed in our U.S. Patent Applications Ser. Nos. 39,337 and 42,219. The reaction of glucose and the immobilized carbohydrate oxidase of *Polyporus obtusus* ATCC #26733 to yield D-glucosone and hydrogen peroxide is coupled to the reaction of immobilized seaweed peroxidase from Coralina sp. in the presence of bromide and propylene to yield propylene bromohydrin. The end result of this coupled reaction, then, is the co-production of glucosone for subsequent fructose production and of propylene bromohydrin, readily converted to propylene oxide as described in Patent Applications Ser. Nos. 39,337 and 42,219. Any enzyme capable of oxidizing the hydroxyl group on the 2-carbon of glucose with associated production of hydrogen peroxide can be coupled to any halogenating peroxidase and the composite used for alkene-halohydrin production following the teachings of our aforereferenced co-pending patent applications.

Cell-free, purified seaweed peroxidase enzyme is prepared as follows:

Coralina sp. obtained along the coast of La Jolla, California, is ground in a Virtis 45 homogenizer for 5 minutes in distilled water. The homogenate is spun at 20,000 rpm for 20 minutes. The supernatant is decanted and saved. The pellet is resuspended in distilled water and recentrifuged. This supernatant and previous supernatant are combined. The solution is brought first to 33%, then to 55% saturation in ammonium sulfate. Centrifugation and separation of pellet is performed at each step. The 33%–55% pellet fraction is passed through a DEAE column using a 0.3 M to 1 M phosphate buffer (pH 6.0) gradient. The fraction which elutes at 1 M is dialyzed against 20 mM phosphate buffer (pH 6) overnight.

The immobilized seaweed peroxidase is prepared as follows:

Glass beads (obtained from Sigma Chemical Company, PG-700-200) are activated by suspending 1 g of glass beads in 18 ml of deionized water. 2 ml of 10% (v/v)α-aminopropyltriethoxy silane are added and the pH of the mixture is adjusted to 3–5 with 6 N HCl. The mixture is shaken at 75° C. for two hours. The glass beads are then vacuum dried overnight at 80° C. 3.2 ml of purified Coralina sp. enzyme, prepared as above, and 50 mg of water soluble cabodiimide are added to the glass beads. The pH is adjusted to 4.5, and the mixture is then shaken at 4° C. overnight. The product (enzyme coated beads) is washed with water. The activity is measured as 2 monochlorodimedon units/g of beads.

Immobilized carbohydrate oxidase on agarose is prepared as in Example I from 10 ml of cell-free, purified enzyme.

A reaction mixture containing the following ingredients is set up in a 100 ml Pyrex flask:
(a) 1 g seaweed peroxidase coated glass beads,
(b) the immobilized carbohydrate oxidase prepared above,
(c) 800 mg potassium bromide, and
(d) 20 ml of 0.01 M potassium phosphate buffer, pH 7.0.

Both propylene and oxygen are bubbled into the flasks continuously. The reaction is initiated with 1 gm glucose. After 20 hours the reaction is sampled and analyzed for residual glycose, D-glucosone, and propylene bromohydrin. The produced propylene bromohydrin is analyzed as follows:

5 μl of the reaction mixture is injected into a Hewlett-Packard Model 402 gas chromatograph, equipped with a 6-foot by ⅛-inch glass column, packed with Porapak R (80/100 mesh). Flow rate is set at 30 ml/minute for helium and the column temperature is set at 200° C. Retention times for the propylene bromohydrins are 9 minutes for 1-bromo-2-propanol and 10 minutes for 2-bromo-1-propanol.

Product identity is confirmed by comparison with authentic samples of propylene bromohydrin: 1-bromo-2-propanol is purchased from Pfaltz and Bauer, Inc.; 2-bromo-1-propanol is synthesized by lithium aluminum hydride reduction of 1-bromopropionyl chloride. The reaction products and the authentic samples show the same retention times and identical mass spectra: bromine is identified by the presence of the M and M+2 isotope clusters of equal intensity; the molecular ion for both isomers is confirmed by chemical ionization with isobutane reagent gas (M+; m/e 138+140); for 1-bromo-2-propanol the major fragmentation is the expected loss of $CH_2Br$, while for 2-bromo-1-propanol the major fragmentation is the expected loss of $CH_3CHBr$.

The analysis of the sample showed >99% conversion of glucose to D-glycosone and propylene bromohydrin production at 20 gm/l.

EXAMPLE VIII

This example serves to further illustrate the concepts set forth and shown in Example VII. In this instance, immobilized glucose-2-oxidase is substituted for immobilized carbohydrate oxidase.

The immobilized seaweed peroxidase enzyme is prepared as in Example VII. The immobilized glucose-2-oxidase is prepared as in Example VI.

A reaction mixture is set up as in Example VII, substituting immobilized glucose-2-oxidase for immobilized carbohydrate oxidase.

After 20 hours, the reaction is sampled and analyzed for residual glucose. D-glucosone, and propylene bromohydrin. The results showed >99% conversion of glucose to D-glucosone and propylene bromohydrin production at 19.5 gm/l.

EXAMPLE IX

This example illustrates high conversion of glucose to D-glucosone over an extended time period using immobilized carbohydrate oxidase in a column reactor.

Carbohydrate oxidase (cell-free, purified enzyme) (10 ml), prepared as in Example I, is immobilized on hydroxyapatite (calcium phosphate hydroxide) as follows:

To 100 ml of cell-free, purified enzyme, 20 g of hydroxyapatite in 100 ml of 1 mM potassium phosphate buffer at pH 7.0 is added. The mixture is stirred for 30 minutes, then the solids are separated from the liquid by decanting, and the solids washed first with 200 ml of 10 mM potassium phosphate buffer at pH 7.0, then with 200 ml of distilled water.

This material is then packed in a glass column (0.5 cm×4.5 cm). A 1% glucose solution is passed through the column at a flow rate of 1.5 ml per hour. The eluant is periodically analyzed for residual glucose and produced D-glucosone.

The eluant, continuously produced in 5 days of running, showed that >95% of the glucose was converted to D-glucosone. No hydrogen peroxide was detected. The study was terminated before the true enzyme half-life was determined. At the slow flow rate of this experiment both oxygen availability and absence of accumulated hydrogen peroxide contributed to the substantially complete conversion of glucose to D-glucosone. In this case the supporting matrix, hydroxyapatite, caused hydrogen peroxide decomposition.

It may be seen, therefore, that the invention represents the first commercially feasible method for converting glucose to fructose which does not require expensive steps for the separation of glucose and fructose. Each of the process steps may be carried out easily at room temperature and atmospheric pressure, thus minimizing the energy requirements if desired. By-products of the process are not difficult to dispose of or utilize, and the major product is substantially pure fructose which may easily be obtained in crystalline form.

Various modifications of the invention in addition to those shown and described herein will become apparent to those skilled in the art from the foregoing description and accompanying drawings. Such modifications are intended to fall within the scope of the appended claims.

What is claimed is:

1. A method for making fructose from glucose, comprising, providing an aqueous solution of D-glucose, converting at least about ninty-five percent of the D-glucose in solution to D-glucosone in solution by enzymatic oxidation while removing or utilizing co-produced hydrogen peroxide, and hydrogenating the D-glucosone to D-fructose.

2. A method according to claim 1 wherein the D-fructose is recovered in crystalline form.

3. A method according to claim 2 wherein the D-fructose is recovered by evaporation.

4. A method according to claim 2 wherein the D-fructose is recovered by precipitation.

5. A method according to claim 2 wherein the D-glucosone in solution is recovered as a syrup and is resolubolized in an organic solvent, and wherein the hydrogenation of the D-glucosone causes direct precipitation of fructose crystals.

6. A method according to claim 1 wherein the enzyme comprises an oxidoreductase having glucose-2-oxidase activity.

7. A method according to claim 6 wherein the enzyme is selected from the group consisting of glucose-2-oxidase from *Aspergillus oryzae* and carbohydrate oxidase from *Polyporus obtusus*.

8. A method according to claim 6 wherein the enzyme is immobilized.

9. A method according to claim 1 wherein the hydrogen peroxide is removed by enzymatic decomposition by catalase.

10. A method according to claim 1 wherein the hydrogen peroxide is utilized in a co-process.

11. A method according to claim 1 wherein the hydrogenation step is catalyzed by a hydrogenation catalyst selected from the group consisting of the Group VIII elements, the metallic elements of Groups IB and IIB and the transition elements chromium, tungsten and manganese.

12. A method according to claim 11 wherein the hydrogenating catalyst comprises palladium on a support.

13. A method for making crystalline fructose from glucose, comprising, providing an aqueous solution of D-glucose, converting at least about ninty-five percent of the D-glucose in solution to D-glucosone in solution by utilizing an immobilized oxidoreductase enzyme having glucose-2-oxidase activity while removing or utilizing co-produced hydrogen peroxide, hydrogenating the D-glucosone to D-fructose, and recovering the D-fructose in crystalline form.

14. A method according to claim 12 which is carried out in a column reactor.

* * * * *

UNITED STATES PATENT AND TRADEMARK OFFICE
CERTIFICATE OF CORRECTION

PATENT NO. : 4,246,347
DATED : January 20, 1981
INVENTOR(S) : Saul L. Neidleman, et al.

It is certified that error appears in the above-identified patent and that said Letters Patent are hereby corrected as shown below:

Column 9, line 32, "ml" should be --mg--.

Column 9, line 39, "$R_5$" should be --$R_t$--.

Column 10, line 12, "carrier" should be --stirrer--.

Column 12, line 53, "glycose" should be --glucose--.

Column 13, line 11, "glycosone" should be --glucosone--.

Signed and Sealed this

Eleventh Day of August 1981

[SEAL]

Attest:

Attesting Officer

GERALD J. MOSSINGHOFF
Commissioner of Patents and Trademarks